United States Patent [19]

Betts

[11] 4,356,720

[45] Nov. 2, 1982

[54] BURST-PRESSURE TEST FIXTURE FOR PRESSURE VESSELS DYNAMIC ROCKET MOTORS

[75] Inventor: Robert E. Betts, Huntsville, Ala.

[73] Assignee: The United States of America as represented by the Secretary of the Army, Washington, D.C.

[21] Appl. No.: 231,206

[22] Filed: Feb. 4, 1981

[51] Int. Cl.³ .......................................... G01M 19/00
[52] U.S. Cl. .......................................... 73/37; 73/167
[58] Field of Search ................. 73/37, 49.2, 49.7, 116, 73/118 R, 167, 35

[56] References Cited

U.S. PATENT DOCUMENTS

| 3,377,841 | 4/1968 | Neal | 73/49.7 X |
| 3,465,572 | 9/1969 | Covert | 73/49.2 |
| 3,750,459 | 8/1973 | Williams et al. | 73/37 X |
| 4,149,404 | 4/1979 | White | 73/49.7 |

Primary Examiner—Edward R. Kazenske
Assistant Examiner—Joseph W. Roskos
Attorney, Agent, or Firm—Nathan Edelberg; Robert P. Gibson; Jack W. Voigt

[57] ABSTRACT

A method for burst testing a vented pressure vessel accurately measures the true burst pressure of the vented pressure vessel. The method employs a burst-pressure test fixture which comprises a plug and a gauge adapter member for substantially plugging the vent opening in a pressure vessel to be burst tested. The plug and gauge adapter member is adapted for receiving a transducer or pressure gauge that is integrally mounted with a pressure gauge tube which is insertably mounted in the plug and gauge adapter member. The vent opening which is substantially plugged with the tube member of the plug and gauge adapter member is free from stress during pressurization to burst pressure. The method requires that the plug and gauge adapter member be stationary, but the vented pressure vessel is allowed to move outwardly along the tube member during dynamic testing. The fit of the plug to the vent opening (i.e., the throat when the pressure vessel is a rocket motor) is a close enought fit as long as the fly off time of the pressure vessel is greater than the pressure rise time to burst pressure. The fixed position of the plugging member is independent of the pressure vessel during dynamic testing thus allowing the burst pressure that is measured to be the true burst pressure for the vented pressure vessel since the additional forces normally encountered during static testing where the plugging member and vented pressure vessel are stationary are not present in this method.

4 Claims, 4 Drawing Figures

BURST-PRESSURE TEST FIXTURE FOR PRESSURE VESSELS DYNAMIC ROCKET MOTORS

DEDICATORY CLAUSE

The invention described herein may be manufactured, used, and licensed by or for the Government for governmental purposes without the payment to me of any royalties thereon.

BACKGROUND OF THE INVENTION

The field of this invention is in the burst testing of pressure vessels such as rocket motors.

The conventional method of burst testing pressure vessels such as rocket motors is to seal the vessel and apply internal pressure until failure of the vessel occurs. Ths burst pressure is recorded by attaching a gauging system to the vessel or to the pressurizing system. For closed pressure vessels this type of testing poses no problems but for vented vessels, the sealing of the vent puts stress on the vessel in places that would normally not have stress during normal operations. The additional stress induced as a result of sealing of the vent by a closure causes additional forces to be transmitted from the closure to the case of the pressure vessel.

A method of testing of pressure vessels whereby the vent is plugged but in a manner so that the closure or plug is independent of the case of the pressure vessel would be advantageous because the true burst pressure of a vented vessel, especially a rocket motor, could be measured under dynamic conditions.

Therefore an object of this invention is to provide a burst-pressure test fixture having a plug member that serves to substantially plug the vent opening of a pressure vessel during dynamic testing whereby the pressure vessel is free to move in an outward direction from the plug member during pressurization to a burst pressure.

Another object of this invention is to provide a burst-pressure test fixture that employs a combination pressure gauge, plug, and tube member which performs the functions of substantially plugging the vent opening of a pressure vessel being tested, measuring the pressure, and providing a tube down which the pressure vessel can move during pressurization to burst pressure during dynamic testing.

A further object of this invention is to provide a method of determining the burst pressure of a pressure vessel under dynamic conditions.

SUMMARY OF THE INVENTION

The burst-pressure test fixture of this invention is comprised of a plug and gauge adaptor member for substantially plugging the vent opening in a pressure vessel to be burst tested and for receiving a pressure transducer or gauge that is integrally mounted with a gauge tube which is insertably mounted in plug and gauge adapter member. A support member is provided for securing the plug and gauge adapter having the pressure transducer or gauge integrally mounted with a gauge tube. The plug and gauge adapter serves to plug the vent opening but the plug is independent of the pressure vessel.

The burst-pressure test fixture permits the pressure vessel such as a rocket motor to move outward along the plug and gauge adapter member to reach a burst pressure prior to exiting the length of the plug and gauge adapter member. The burst pressure is measured by the pressure transducer or pressure gauge to give a true burst pressure during dynamic conditions.

DESCRIPTION OF THE PREFERRED EMBODIMENT

The burst-pressure test fixture of this invention enables the vent opening of a vented pressure vessel to be substantially sealed or plugged so that the plug is independent of the vented pressure vessel.

Figure 1:
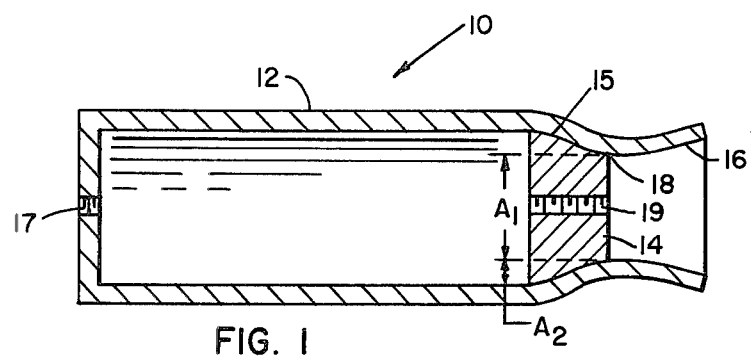
FIG. 1 of the drawing depicts a vented pressure vessel for burst-pressure testing in accordance with the prior art method wherein the vent opening is plugged and stress on the vessel is produced as a result of the internal pressure exerted on the closure plug which is subsequently transmitted to the pressure vessel case.

In further reference to the Figures of the drawing, FIG. 1 shows a vented pressure vessel 10 having a case 12 for burst-pressure testing in accordance with the prior art method which employs a closure member 14 for plugging the vent opening defined by the nozzle 16 and particularly, as defined at the throat 18. An opening 19 is provided in the closure member 14 for the nozzle and a similar opening 17 is provided in the opposite end of the vented pressure case for either positioning a pressure measuring device or for admitting fluid pressure during pressurization to accomplish bursting of pressure vessel. When the vented pressure vessel is a rocket motor, pressurization is generally effected by igniting a propellant within the rocket motor by means of an igniter, both of which are not shown.

Figure 2:
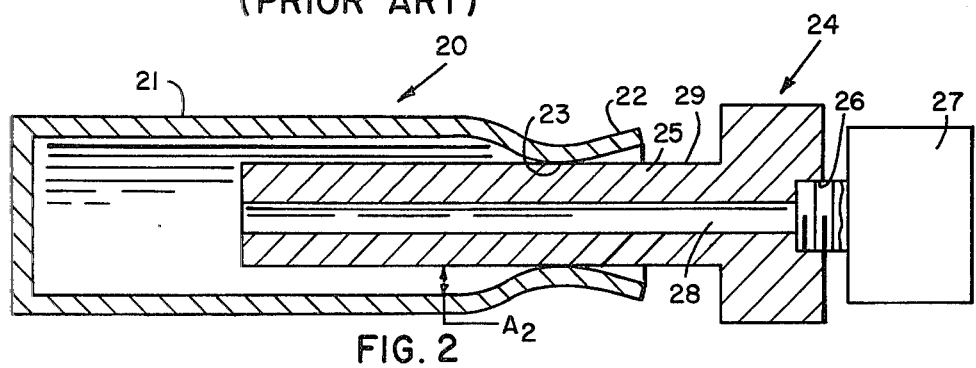
FIG. 2 of the drawing depicts a vented pressure vessel for burst-pressure testing employing the method and device of this invention wherein the plug is independent of the pressure vessel.

FIG. 2 of the drawing depicts a vented pressure vessel 20 comprising a case 21, nozzle 22, and throat 23. A plug and gauge adapter member 24 comprising a tube portion 25 and adapter portion 26 for receiving a pressure sensor is shown inserted through the throat to substantially plug the vent opening defined by throat of the nozzle. A coating of silicon grease 29 is applied to the tube portion 25 of the plug and gauge adapter to facilitate insertion through the throat and also to permit easy travel in a fly off mode during dynamic testing conditions. A pressure detecting means 27 is shown with a pressure communication channel 28 located in the plug and gauge adapter member. When the vented pressure vessel is a rocket motor, pressurization is effected by igniting a propellant within the vented pressure vessel (e.g., rocket motor case) by means of an igniter, both of which are not shown.

The burst-pressure test fixture of this invention provides a means of detecting the true burst-pressure of vented pressure vessels under dynamic conditions. Burst testing of a vented pressure vessel, such as a rocket motor as noted earlier, has been accomplished by the prior art method wherein the vent is sealed and internal pressure is applied until failure of the vessel occurs. The burst pressure is recorded by attaching a gauging system to the vessel or to the pressurizing system. For closed pressure vessels the described type of testing poses no problems but for vented vessels, the sealing of the vent stresses places of the vessel that would not be normally stressed during normal operations.

With additional reference to the drawing in FIG. 1 and for a given internal pressure, the force exerted on the closure is transmitted to the case along the surface of contact 15 of the closure with the case. If the closure were not present, the force on the area designated as $A_2$, which would actually be exerted along 15, would be less, for example, the force on $A_2$ without closure: $F = PA_2$; the force exerted along the surface 15 with closure: $F = P(A_2 + A_1)$. The surface 15 is further defined as the portion of the internal surface of the case where convergence begins toward the nozzle section and ends at the throat of the nozzle section.

When the vent opening is plugged in accordance with method as shown in FIG. 2 the plug is independent of the pressure vessel; therefore, the force on $A_2$ does not change even if the plug is in or removed. A further description of the invention is as follows: A plug is inserted through the vent opening of the pressure vessel, in this instance the rocket motor nozzle throat. The gauging system is attached to the plug and gauge adapter. The fit of the plug to the throat need not be a close fit, as long as the fly off time of the vessel is greater than the pressure rate rise time to burst pressure. Factors which influence the design are the mass of the vessel, the burst pressure of the vessel, the length of the vessel, the length of the plug into the vessel, and the pressure rate rise within the vessel.

EXAMPLE

An example of a successful test is as follows: A small rocket motor of about $1\frac{1}{2}$ inches long was inserted on to a plug and gauge adapter tube of about $1\frac{1}{8}$ inches long. The mass of the motor was about 20 grams. The motor was pressurized at a rate of about 5,000,000 psi/sec. The motor flew up the plug and gauge adapter tube for about $\frac{1}{2}$ inch in about 0.001 seconds then bursted (See FIG. 3 and the additional description below).

Figure 3:
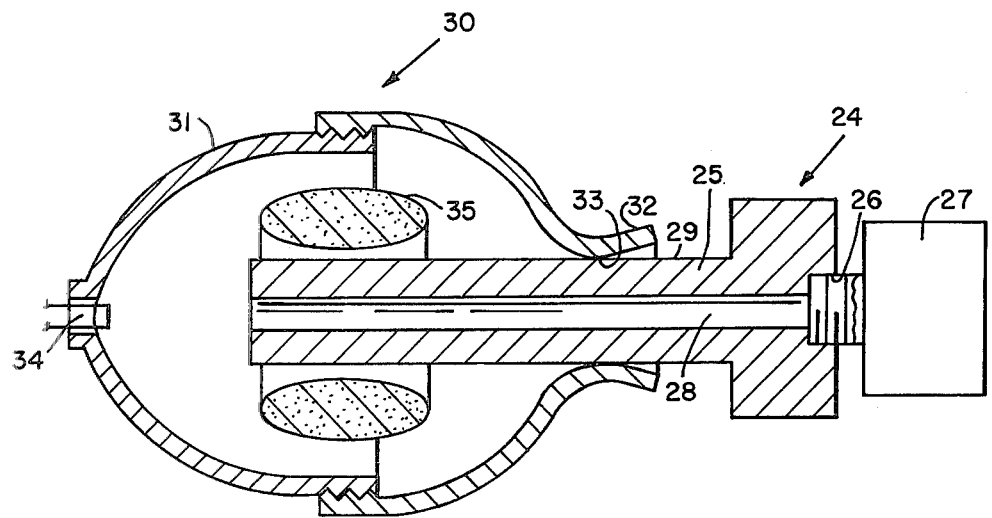
FIG. 3 of the drawing depicts a small rocket motor on a plug and gauge adapter which serves to substantially plug the vent opening (i.e. the throat of the nozzle) of the rocket motor undergoing burst-pressure testing.

FIG. 3 depicts a vented pressure vessel 30 in the form of a rocket motor comprising a case 31, nozzle 32, and throat 33. A plug and gauge adapter member with assigned numerals as set forth in FIG. 2 is shown positioned through the throat. Igniter means 34 for propellant 35 is shown positioned in the end of rocket motor and within the rocket motor respectively. The ignition of the propellant produced pressurization at a rate of 5,000,000 psi/sec which resulted in bursting the rocket motor in about 0.001 seconds after traveling down the plug and gauge adapter tube for about $\frac{1}{2}$ inch.

Figure 4:
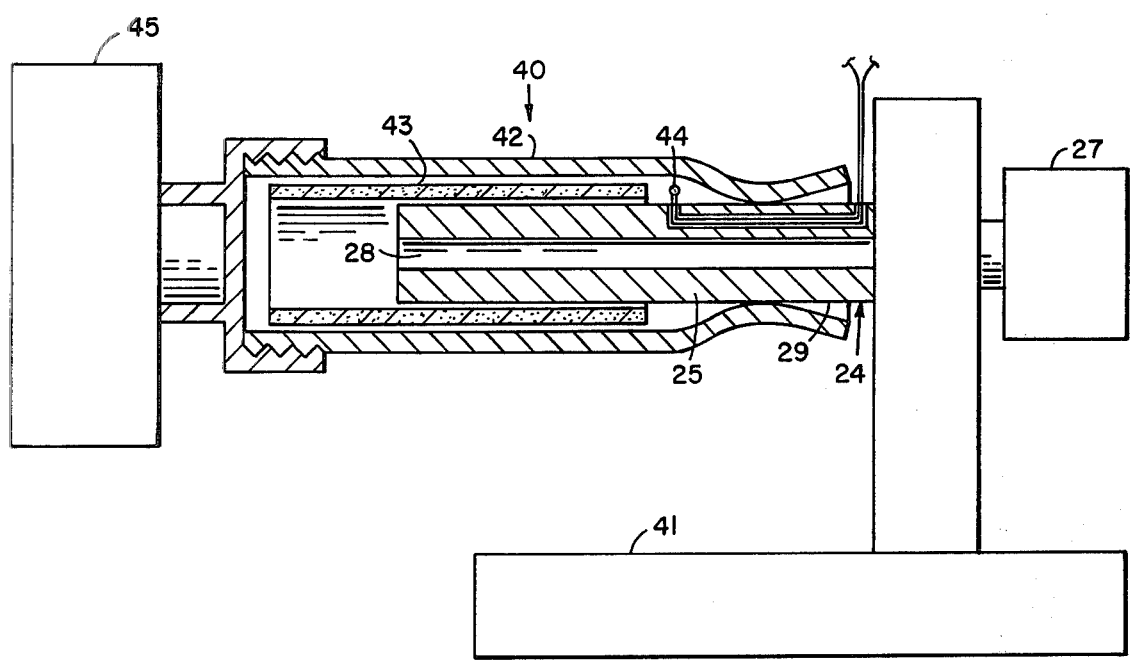
FIG. 4 of the drawing depicts a dynamic motor case burst tester which simulates all flight environments without load forces due to static loads.

FIG. 4 depicts a dynamic rocket motor case burst tester 40 which simulates all flight environments without load forces due to static load. The plug and gauge adapter member with assigned numerals as set forth in FIGS. 2 and 3 is shown positioned through the throat and secured to a base plate 41. The rocket motor case 42 contains propellant 43 and igniter means 44 for igniting the propellant for pressurization of the rocket motor case. A flying mass portion 45 is shown secured at the end of rocket motor. In this particular embodiment, a flying mass portion weighing 1010 grams less other rocket parts was the predetermined weight required to control fly off of the rocket motor case during dynamic testing. This is one of the parameters of the design for a particular rocket motor. Other parameters include the burst pressure of the vessel, the length of the vessel, the length of the plug and gauge adapter tube member inserted through the throat, and the pressure rate rise within the vessel as determined by the propellant burning rate.

I claim:

1. In a vented pressure vessel having a tubular plug and guage adapter member provided with a pressure gauge therein for measuring the pressurization to burst pressure, said tubular plug and gauge adapter for insertion into the vent opening of said vented pressure vessel for substantially plugging said vent opening during burst testing, the method of burst testing said vented pressure vessel having an internal means for pressurization comprising the steps of:
   (i) mounting said plug and gauge adapter in a stationary position so that said tubular member is horizontally positioned;
   (ii) inserting a pressure gauge that is integrally mounted with a pressure gauge tube member into said plug and gauge adapter member;
   (iii) coating said tubular member of said plug and gauge adapter member with a silicon lubricant to facilitate the positioning of a vented pressure vessel on said tubular member while substantially plugging the vent opening of said vented pressure vessel;
   (iv) positioning a vented pressure vessel to be burst tested on said silicon lubricated tubular member, said vent opening of said plug and gauge adapter member being substantially plugged by said tubular member, said vented pressure vessel being provided with means for pressurization that is mounted within said vented pressure vessel; and,
   (v) pressurizing said vented pressure vessel at a predetermined rate to effect bursting of said vented pressure vessel as said vented pressure vessel is moving at a predetermined rate in an outward direction along said tubular member, said bursting being effected prior to said vented pressure vessel exiting from said tubular member; and,
   (vi) measuring said pressure at which bursting of said vented pressure vessel takes place which is the true burst pressure of said vented pressure vessel tested under dynamic conditions.

2. The method as set forth in claim 1 wherein said vented pressure vessel is in the form of a rocket motor having a vent opening which is defined by the throat section of said rocket motor nozzle and wherein said pressurization rate is about 5,000,000 psi/sec to effect bursting of said vented pressure vessel in about 0.001 second after said vented pressure vessel traveled outward along said tubular member for a distance of about $\frac{1}{2}$ inch.

3. The method as set forth in claim 1 wherein said vented pressure vessel is in the form of a rocket motor having a vent opening which is defined by the throat section of said rocket nozzle and wherein said rocket motor has a flying mass attached to forward end of said rocket motor, said flying mass being of a predetermined weight to control the time of movement in said outward direction along said tubular member so that said time of movement is greater than said pressurization rate rise time to burst pressure.

4. A burst-pressure test fixture for testing a vented pressure vessel under dynamic conditions, said burst-pressure test fixture comprising:
  (i) a tubular plug and gauge adapter member having a tubular portion with an inner diameter adapter portion for receiving a pressure gauge and tube member which is insertably mounted within said tubular plug and gauge member, said tubular portion having an outer diameter for substantially plugging the vent opening during burst testing of said vented pressure vessel under dynamic conditions;
  (ii) a pressure gauge and tube member insertably mounted within said tubular plug and gauge adapter member, said pressure gauge and tube member being responsive to pressurization of said vented pressure vessel by an internal means for pressurization mounted within said vented pressure vessel, said pressure gauge and tube member being also responsive to pressurization as said vented pressure vessel moves outwardly along said tubular plug in response to initiation of said means for pressurization mounted within said vented pressure vessel, said pressure gauge and tube member being additionally responsive to the burst pressure that is reached during a pressure rate rise time to burst pressure, said pressure rate rise time to burst pressure being less than the time that said vented pressure vessel moves along said tubular member responsive to said pressurization.

* * * * *